United States Patent [19]

Stalling et al.

[11] 4,026,917
[45] May 31, 1977

[54] METHOD OF REMOVING POLYNUCLEAR AROMATIC COMPOUNDS BY ADSORPTION WITH COCONUT CHARCOAL

[75] Inventors: David L. Stalling; James N. Huckins, both of Columbia; James L. Johnson, Fulton, all of Mo.

[73] Assignee: The United States of America as represented by the Secretary of the Interior, Washington, D.C.

[22] Filed: Feb. 11, 1975

[21] Appl. No.: 549,127

[52] U.S. Cl. .................. 260/473 G; 260/520 C
[51] Int. Cl.² .................................. C07C 69/76
[58] Field of Search .................. 260/473 G, 520 C

[56] References Cited

OTHER PUBLICATIONS

Nishiyama, Y. et al. Chem. Abst. 208082z vol. 83, 1975.

Mihara, O. Chem. Abst. 45902e vol. 82, 1975.

*Primary Examiner*—Paul J. Killos
*Attorney, Agent, or Firm*—William S. Brown; Donald A. Gardiner

[57] ABSTRACT

Polynuclear aromatic compounds are irreversibly adsorbed by coconut charcoal and are separated from desired constituents by treatment in a coconut charcoal column. This invention is particularly valuable in providing a method suitable for large scale use for removing dioxins and other undesirable polynuclear aromatic hydrocarbons which are found as impurities in small but highly toxic amounts in industrial compounds and herbicides such as 2,4,5-T, 2,4-D and derivatives thereof.

8 Claims, No Drawings

METHOD OF REMOVING POLYNUCLEAR AROMATIC COMPOUNDS BY ADSORPTION WITH COCONUT CHARCOAL

BACKGROUND OF THE INVENTION

Much of the following background material is found in REPORT ON 2, 4, 5-T, A Report of The Panel Of The President's Science Advisory Committee, Executive Office of the President, Office of Science and Technology, March 1971.

The herbicide 2,4,5-trichlorophenoxyacetic acid, commonly known as 2,4,5-T has the chemical formula:

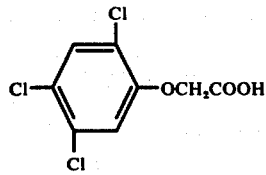

The usual starting material in the chemical synthesis of 2,4,5-T is 1,2,4,5-tetrachlorobenzene which can be reacted with methanol and sodium hydroxide in an autoclave under high temperature and pressure conditions to give the sodium salt of 2,4,5-trichlorophenol:

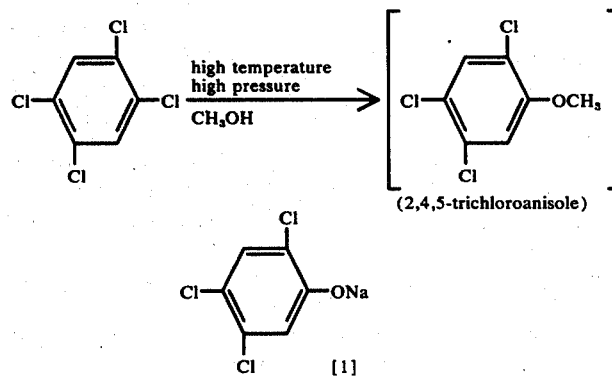

2,4,5-trichloroanisole is presumed to be an intermediate in this reaction. The high temperature and high pressure conditions of this step are also favorable for the production of a variety of other compounds from these starting materials. The choice of the proper temperature and pressure, and the control of these conditions throughout the reaction are critical for minimizing side reactions and hence impurities in the final product.

One trace impurity produced in the manufacture of 2,4,5-T has received considerable attention. Tetrachlorodibenzo-p-dioxin, commonly known as TCDD

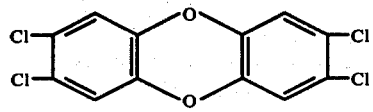

is produced as a side product under the conditions of Step (1). This compound is known to be extraordinarily toxic. Therefore, while TCDD generally appears in only minute amounts in 2,4,5-T, its presence even in such small amounts has generated extreme concern.

A clue to the possible origin of the dioxins was suggested in their synthesis by condensation, Tomita, M., Veda, S. and Narisada, M. Yakugaka Zasshi 79:186, 1959. Two molecules of 2,4,5-trichlorophenol condense directly to give TCDD:

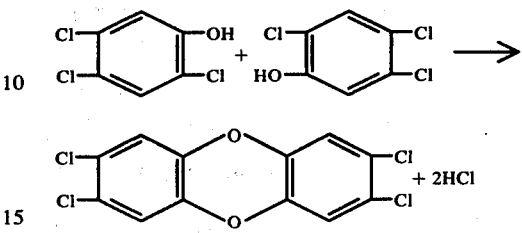

Two molecules of 2,4-dichlorophenol condense to give the dichlorodibenzo-p-dioxin,

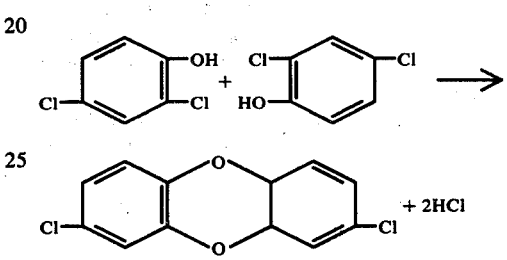

and mixtures of various isomeric chlorinated phenols give mixed chlorinated dioxins. Thus, corresponding dioxins can be formed in the preparation of other herbicides related to 2,4,5-T, for example 2,4-dichlorophenoxyacetic acid, commonly known as 2,4-D. The members of the dioxin family are considered dangerous, in general, and therefore their removal from herbicides or the suppression of their formation in the first place has received considerable attention. Progress has been made particularly in varying conditions in the manufacturing process so that it has been possible to produce 2,4,5-T having levels less than 1ppm. of dioxins. Nevertheless, a need exists for a method of further reducing dioxin levels and for purifying samples containing dioxin in amounts substantially greater than 1 ppm. A particular need exists for a method for reducing dioxin levels in 2,4,5-T, 2,4-D and the like to less than 1 ppm which is suitable for large scale application. The concern over the presence of even small amounts of dioxins on the order of 1 ppm arises both because of the high toxicity of the dioxins and the fact that dioxins tend to be fat soluble and non-biodegradable. Thus, dioxins tend to concentrate in animal fatty tissue.

Incident to our work in removing halogenated aromatic compounds from liquids by chromatographic techniques, it was observed that dioxins, and TCDD in particular, are irreversibly adsorbed on coconut charcoal. Subsequently, it was found that a variety of polynuclear aromatic compounds including dichloro-, trichloro-, tetrachloro- and octachloro-dibenzo-p-dioxins, chlorinated naphthalenes and dibenzofurans are also irreversibly adsorbed on coconut charcoal. The irreversible adsorption on coconut charcoal is not entirely understood but it has been found that the foregoing materials cannot be recovered when adsorbed on coconut charcoal by using extended solvent extraction or displacement.

It is known that some charcoals will preferentially adsorb aromatic organic compounds and this is attributed to the electronic affinity of the aromatic ring for the surface of carbon, in the form of graphite in particular. Synder, R., Principles of Adsorption Chromotography, Marcel Dekka, Inc., New York, 1968, pp. 168–169. However, such adsorption is usually reversible and is typified by our experience with Darco charcoal which reversibly adsorbs the polynuclear aromatic compounds mentioned above which are irreversibly adsorbed on coconut charcoal.

BRIEF DESCRIPTION OF THE INVENTION

Our finding that coconut charcoal will irreversibly adsorb polynuclear aromatic compounds such as dichloro-, trichloro-, tetrachloro-, and octachloro-dibenzo-p-dioxins, chlorinated naphthalenes and dibenzofurans led us to this invention which relates to the removal of polynuclear aromatic compounds from mixtures containing polynuclear components and other components which are not irreversibly absorbed. Accordingly, in brief, this invention constitutes the method of removing polynuclear aromatic compounds from mixtures which contain constituents other than polynuclear aromatic compounds by contacting the mixture with coconut charcoal for a period of time and under conditions effective to cause irreversible adsorption of said polynuclear aromatic compounds on the coconut charcoal. The means by which contact of the mixture to be separated and the coconut charcoal is effected is not extremely critical. It has been found that percolating the mixture through a column packed with granular charcoal is both convenient and effective.

Other methods such as stirring charcoal in the mixture to be purified were almost as effective as the column but required a longer contact time. The mixture can be passed through the column as is or it can be diluted with a suitable solvent. It is sometimes desirable to utilize a heated column such as the steam heated column used in the example described below.

This invention is broadly applicable to the removal of polynuclear aromatic compounds from mixtures containing components other than a polynuclear aromatic component. However, the invention is particularly well-suited for removal of polynuclear aromatic compounds which are present in minor amounts especially very small amounts on the order of 1000 ppm, or less. Also, since the adsorption by coconut charcoal is irreversible, the invention is especially suited in those circumstances where there is no desire to recover the polynuclear aromatic compound which is removed.

In view of the foregoing, the invention finds particular applicability in the removal of undesirable dioxin compounds which appear as contaminants in herbicides such 2,4,5-T (2,4,5-trichlorophenoxyacetic acid), 2,4-D (2,4-dichlorophenoxyacetic acid) and derivatives thereof such as the esters. The dioxin contaminants in such herbicides occur in amounts on the order of 50 ppm to 1 ppm or less and it is desirable to reduce the amount of the dioxins to levels significantly below 1 ppm.

A specific and particularly valuable application of this invention is in the removal of dioxins, particularly TCDD (tetrachlorodibenzo-p-dioxin) from the herbicide Orange which is a 1:1 (by weight) mixture of the butyl esters of 2,4-D and 2,4,5-T.

A variation in this process which has been found to be advantageous especially where the mixture to be treated contains polynuclear contaminants in excess of about 100 ppm is to conduct a pretreatment step or steps constituting adsorption with conventional charcoal such as Darco charcoal. Although charcoals other than coconut charcoal do not result in irreversible adsorption such pretreatments are effective in lowering the level of polynuclear contaminants and the use of other charcoals for preliminary treatment has the advantage of reducing the amount of coconut charcoal required.

The use of solvent diluents is recommended if the adsorption is not conducted at an elevated temperature. If solvent is used, the solvent is preferably a non-aromatic solvent which is miscible with or dissolves the mixture being treated. Suitable solvents include acetone, petroleum ether, cyclohexane, diethyl ether, dichloromethane, ethyl acetate, water and the like. Polar solvents are generally preferred over non-polar or aromatic solvents. Elevated temperatures in the range of 75° to 150° C are sometimes beneficial especially where solvent diluents are not used.

DETAILED DESCRIPTION OF THE INVENTION

This invention is illustrated by the following specific examples conducted with herbicide Orange a 1:1 (by weight) mixture of the butyl esters of 2,4-dichlorophenoxyacetic acid and 2,4,5-trichlorophenoxyacetic acid.

EXAMPLE 1

A column was prepared by adding 1.5 g. of activated coconut charcoal to an all glass 1.0 cm. i.d. × 10 cm. long column. The charcoal was supported in the column by glass wool and 1 cm of acid washed Ottawa sand. The charcoal was also covered by 1.0 cm of Ottawa sand to prevent the charcoal from floating in the percolating solvent.

A 25 ml. sample of the herbicide Orange containing 15 ppm dioxin was diluted to 250 ml in acetone (25/225) and percolated through a fresh 1.5 g coconut charcoal column and the solvents removed. The dioxin content of the concentrated sample is entered in Table 1 below along with the results of the following examples.

EXAMPLE 2

Example 1 was repeated except that a second percolation was conducted in the same column instead of a fresh column.

EXAMPLE 3

A 50/50 (v/v) solution of the herbicide Orange was stirred on a magnetic stirrer with acetone for 1 day. Then an additional 1 g of coconut charcoal was added and stirring was continued for another day. The solvent was removed and the sample analyzed for dioxin as in Example 1. The results are recorded in Table I below.

EXAMPLE 4

Example 1 was repeated except that the feed solution consisted of 50 ml of the herbicide Orange diluted to 1 liter with acetone.

EXAMPLE 5

To a 14/20 T ground glass condensor (i.d. about 1 cm.) which had previously been fitted with a plug of glass wool, there was added 1.5 g of activated coconut charcoal.

The condensor was clamped in a vertical position and the outer condenser jacket was connected to a live steam source. After placing a layer of glass wool above the charcoal a 14/20 separatory funnel was fitted above the charcoal and 25 ml of the herbicide Orange added to the funnel. The herbicide was then percolated through the charcoal column (heated to 100° C with steam) and 5 ml aliquots were collected. The first 5 ml aliquot collected is designated (a), the second 5 ml aliquot (b), the third (c) and the fourth (d). The dioxin contents for aliquots (a) – (d) are separately recorded in Table I.

TABLE I (Initial Dioxin Content 15–17 micrograms/gram)

| EXAMPLE | DIOXIN FOUND micrograms/gram | REMOVAL (%) |
| --- | --- | --- |
| 1 | <0.006 | >99 |
| 2 | <0.015 | >99 |
| 3 | <0.85 | 94 |
| 4 | <0.017 | 99 |
| 5(a) | 0.0125 | — |
| 5(b) | 0.050 | — |
| 5(c) | 0.26 | — |
| 5(d) | 0.95 | — |

Having set forth our invention, and several specific embodiments thereof, it will be understood that changes may be made from the specific embodiments set forth without departing from the spirit of the invention exceeding the scope thereof as defined in the following claims.

We claim:

1. A method for separating polynuclear aromatic compounds selected from the group consisting of chlorinated -dibenzodioxins, -naphthalenes, -dibenzofurans and mixtures thereof from a mixture in which the major constituents are other than polynuclear aromatic compounds by passing the mixture through a column containing granular coconut charcoal to cause substantially irreversible adsorption of said polynuclear aromatic compounds.

2. The method of claim 1 wherein said mixture contains said polynuclear aromatic compounds in an amount of 1000 ppm by weight or less of the total mixture.

3. The method of claim 1 in which said mixture comprises 2,4-dichlorophenoxyacetic acid, 2,4,5-trichlorophenoxyacetic acid, the lower alkyl esters of said acids or the amine salts of said acids and said polynuclear aromatic compounds are chlorinated dibenzo-p-dioxins.

4. The method of claim 3 wherein said mixture is a 1:1 (weight) mixture of the butyl esters of 2,4-dichlorophenoxyacetic acid and 2,4,5-trichlorophenoxyacetic acid.

5. The process of claim 1 in which said mixture is passed through said column more than once.

6. The process of claim 1 in which said mixture is pretreated with activated carbon other than coconut charcoal prior to its contact with coconut charcoal.

7. The method of claim 1 in which said mixture is diluted with a solvent from the group consisting of acetone, petroleum ether, cyclohexane, diethyl ether, dichloromethane, ethyl acetate, and water prior to passing through said column, and the column is maintained at ambient temperature.

8. The method of claim 1 in which said mixture is not diluted with a solvent and the column is maintained at a temperature of 75° to 150° C.

* * * * *